United States Patent [19]
Davidson

[11] Patent Number: 5,442,437
[45] Date of Patent: Aug. 15, 1995

[54] SAMPLE CELL AND PROBE FOR SPECTROPHOTOMETER

[75] Inventor: Timothy M. Davidson, Alta Loma, Calif.

[73] Assignee: Atlantic Richfield Company, Los Angeles, Calif.

[21] Appl. No.: 120,263

[22] Filed: Sep. 13, 1993

[51] Int. Cl.$^6$ .......................................... G01N 21/05
[52] U.S. Cl. ........................................................ 356/246
[58] Field of Search ........................................ 356/246

[56] References Cited

U.S. PATENT DOCUMENTS

| | | | |
|---|---|---|---|
| 4,664,522 | 5/1987 | LeFebre | 356/328 |
| 4,988,155 | 1/1991 | Harner et al. | 356/246 |
| 5,078,493 | 1/1992 | Evens et al. | 356/246 |
| 5,140,169 | 8/1992 | Evens et al. | 356/246 |

OTHER PUBLICATIONS

David A. LeFebre and George P. Thomas, "An In-Line Scanning UV-VIS-NIR Process Monitor"; ISA 1985–Paper #85-0033.

Primary Examiner—Richard A. Rosenberger
Attorney, Agent, or Firm—Michael E. Martin

[57] ABSTRACT

A flow cell and probe member apparatus for a spectrophotometer type analyzer for fluids such as petroleum fuel blends using the absorbance characteristics of electromagnetic radiation in the ultra violet/visible light/near infrared portion of the spectrum includes a body having opposed branch parts which define a flow passage for the fluid to be analyzed and including opposed connector parts for connecting the body to fluid transmitting conduits. Opposed waveguide probes project into the flow path from opposed supporting branch parts of the cell body which have opposed surfaces which are spaced apart at a predetermined distance to locate the probe members in such a way that the transmission path length of the radiation signal is closely controlled to minimize errors in the absorbance readings. Each of the probe members includes a waveguide portion including a light transmitting window having a self-cleaning surface formed thereon which is held a predetermined distance from a surface on the probe member body which is engageable with the locating surface on the cell body.

1 Claim, 1 Drawing Sheet

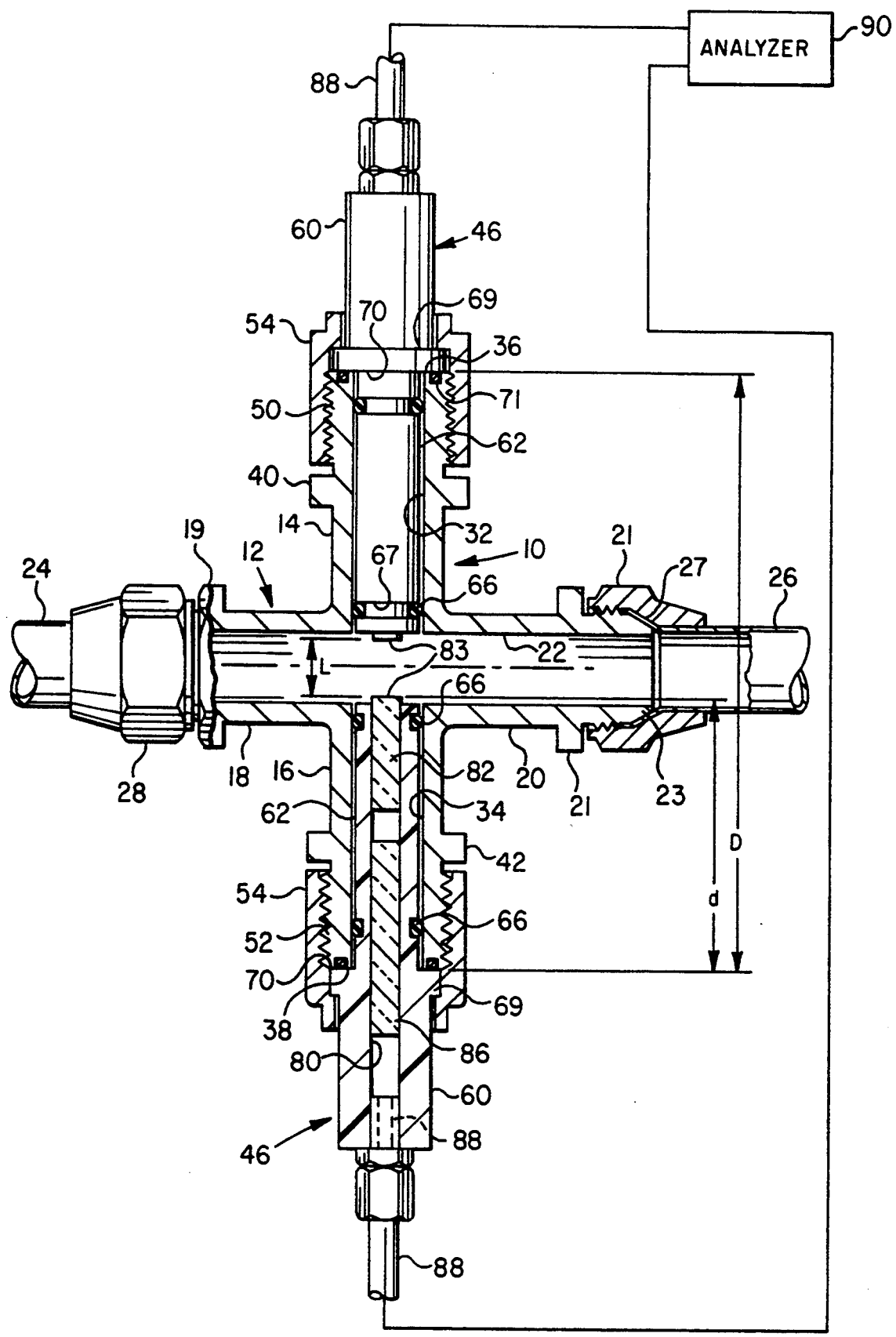

SAMPLE CELL AND PROBE FOR SPECTROPHOTOMETER

BACKGROUND OF THE INVENTION

1. Field of the Invention

The present invention pertains to a flow cell for analyzing fluid samples using a spectrophotometer type analyzer and light transmitting probes which are mounted in the cell to permit some light absorbance by the sample fluid.

2. Background

The development of improved optical fiber type transmission members and fittings has provided for improved chemical and refinery process control using spectrophoto-meter type process analyzers. For example, in the refining of petroleum fuels, there has recently been developed an on-line gasoline octane monitoring system using a process spectrophoto-meter, together with fiber optic waveguides to transmit "light" signals between the instrument and the process stream. A sample flow cell and probe arrangement monitors a sample flowstream of the gasoline blend whereby a "light" beam or signal in the ultra violet-visible light-near infrared (UV/Vis/NIR) portion of the spectrum is passed through the gasoline sample flowstream and the gasoline selectively absorbs some near infrared components of the light beam based on its specific chemical composition. The strength of this absorption phenomena can then be related to the sample octane number, for example.

However, one problem with sample probes for spectrophotometers which monitor radiation in the UV/-Vis/NIR portion of the spectrum is that the spacing between the light signal transmitting probe members or the so-called sample path length is not adequately controlled. Since the amount of light absorption is proportional to the path length of light passing through the sample being analyzed, the spacing of the path length or the distance between the light transmitting members of the probe/waveguide circuit must be closely controlled. Known types of sample probes do not provide this important feature in a manner which has been deemed suitable.

Another problem associated with known probes of the general type discussed herein pertains to the tendency of the waveguides to become clouded or dirty in use. However, the present invention overcomes some of the deficiencies of known types of sample flow cell/probe arrangements for spectrophotometer type process or sample analyzers, including those mentioned herein.

SUMMARY OF THE INVENTION

The present invention provides an improved fluid sample flow cell and probe apparatus for use in analyzing certain characteristics of a sample of fluid using spectrophotometry in the UV/Vis/NIR portion of the electromagnetic radiation spectrum.

In accordance with an important aspect of the present invention an improved sample cell and probe apparatus is provided wherein the light path length through the sample or the so-called sample path length is closely controlled to eliminate errors from changes in the path length which are known to occur with prior art types of sample cell/probe arrangements.

In accordance with a further aspect of the present invention, an improved sample flow cell and probe apparatus is provided wherein opposed probe members are supported on the apparatus body in such a way as to minimize variations in distance or path length of the light signal which passes through the fluid sample being analyzed and alignment of the optical waveguide members is more closely controlled. The sample cell and probe apparatus also provides for rapid and convenient disconnection of the probe members for replacement or cleaning, if necessary.

In accordance with yet a further aspect of the present invention, a sample cell and probe arrangement is provided wherein the waveguide members exposed to the fluid being analyzed are interposed in the fluid flowpath in such a way as to assure a self-cleaning action by the fluid flowing over the window surfaces of the waveguides so as to minimize contamination or clouding of the surfaces. The waveguide or probe body is adapted to be supported in the fluid sample cell body in such a way as to minimize the amount of fluid remaining in the cell body when the fluid is changed or drained from the apparatus to prevent contamination when new or different fluids are introduced into the apparatus.

Those skilled in the art will further appreciate the above-mentioned features and advantages of the present invention together with other superior aspects thereof upon reading the detailed description which follows in conjunction with the drawing.

BRIEF DESCRIPTION OF THE DRAWING

The drawing FIGURE is a central section view of the unique sample flow cell and probe apparatus of the present invention.

DESCRIPTION OF A PREFERRED EMBODIMENT

In the description which follows, like parts are marked throughout the specification and the drawing FIGURE with the same reference numerals, respectively. The drawing FIGURE is not necessarily to scale.

The unique sample flow cell and probe apparatus of the present invention is generally designated by the numeral 10 in the drawing FIGURE. The apparatus 10 includes a cell body member 12 made of a suitable corrosion resistant material such as stainless steel, monel, Hastelloy C or titanium, for example, if necessary. The cell body 12 includes a pair of opposed and substantially coaxial branch parts 14 and 16 and a second pair of opposed and generally coaxially aligned branch parts 18 and 20 which extend in a direction substantially normal to the branch parts 14 and 16, respectively. A cylindrical fluid flow passage 22 extends through the parts 18 and 20. The parts 18 and 20 are suitably configured at their distal ends, such as shown for the distal end 23 of branch part 20, to provide for connecting fluid flow conduits 24 and 26 to the branch parts 18 and 20, respectively. The configuration of the distal end portions of the branch parts 18 and 20 may be such as to provide for suitable hydraulic fitting connections as illustrated, by way of example only, wherein a flared end 27 of the conduit 26 is secured to the branch part 20 by a suitable nut 28. The conduit 24 is similarly connected to the branch part 18 also by a nut 28. Other forms of fluid tight connections may be provided between the conduits 24 and 26 and the branch parts 18 and 20 of the body 12. Integral collar portions 19 and 21 are provided on the branch parts 18 and 20 and may have suitable hexagonal wrench flats formed thereon for use in connecting the conduits 24 and 26 to the apparatus 10.

The flow passage 22 is intersected by opposed and coaxially aligned bores 32 and 34 formed in the branch parts 14 and 16, respectively. The bores 32 and 34 extend from the passage 22 to respective transverse end faces 36 and 38 formed on the branch parts 14 and 16, respectively. The distance between the faces 36 and 38 as indicated by the dimension "D" is preferably closely controlled in accordance with an important aspect of the present invention. The branch parts 14 and 16 are each also provided with integral collar portions 40 and 42 which also may have suitable wrench flats formed thereon for use in connecting to the body 12 a pair of opposed signal transmitting probe members 46 which will be further described in some detail hereinbelow. The portions of the branch parts 14 and 16 which are distal of the collars 40 and 42 are designated by numerals 50 and 52, respectively, and are externally threaded for receiving suitable retaining nuts 54 which are operable to retain the probe members 46 on the body 12 as illustrated.

Each probe member 46 has a generally cylindrical body member 60 which includes a cylindrical portion 62 of a diameter slightly less than the diameter of the bores 32 and 34. Spaced apart O-ring seals 66 are suitably retained in annular grooves formed in the body portion 62 and are engageable with the bore walls of the bores 32 and 34 to prevent leakage of fluid from the passage 22 out of the body 12. In particular, the seals 66 disposed in the grooves 67 are positioned closely adjacent the intersection of the bores 32 and 34 with the passage 22 to minimize in the volume of the small annular spaces between the bores 32 and 34 and the body portions 62 of the probes 46 and the consequent retention of fluid therein. In this way, contamination of fluid samples of different chemistry is avoided during changeover of use of the sample flow cell and probe apparatus in connection with a spectrophotometer.

The probe bodies 60 are each provided with a transverse collar portion 69 having a reference surface 70 engageable with the respective transverse end faces or surfaces 36 and 38 for locating the probes 46 with respect to the passage 22 in a precise position such that the light signal path length "L" as indicated in the drawing, is controlled to a predetermined amount with minimal tolerance. As illustrated, a suitable annular seal 71 is disposed on the respective body portions 50 and 52 and engageable with the collar portion 69 to serve as a backup seal to prevent leakage of fluid into or out of the body 12. If the integrity of the seals 66 is assured, the seal 71 may be eliminated. In any event, the surfaces 36 and 38 make firm contact with the surfaces 70 on the probe body members 60, respectively.

Each of the probes 46 has a longitudinal central bore 80 extending through the body members 60, as illustrated for one of the probes. Suitable waveguide parts are disposed in the bores 80 for low absorbance transmission of electromagnetic radiation in the UV/Vis/-NIR portion of the spectrum. In this regard, the probes 46 are each provided with a low signal loss and corrosion resistant waveguide part comprising a cylindrical sapphire window 82 suitably retained in the bore 80 by a suitable adhesive, for example. The windows 82 have transverse end faces 83 which are disposed opposite each other and spaced apart by the distance L, as indicated. The probes 46 also each have a suitable lens portion such as a fused silica rod 86 disposed in the bore 80 and a waveguide member 88 which is operably connected to a suitable spectrophotometer or analyzer generally indicated by the numeral 90 in the drawing FIGURE. One of the waveguide 88 and probe 46 assemblies is connected to a source of light in the above-mentioned range of the spectrum for transmission therethrough and across the sample path indicated by the dimension L in the drawing FIGURE whereby the signal as received by the other probe 46 is then returned to the analyzer 90 by the other waveguide 88.

In the analysis of fluids in an on-line process type analyzer application for the analyzer 90 and the flow cell and probe apparatus 10, fluid is typically flowing on a continuous basis through the passage 22 and certain characteristics of the fluid may be continuously or intermittently determined by monitoring the absorbance of the signal transmitted through the waveguides 88 and the probes 46 to and from the analyzer 90 in accordance with known practice. Since the amount of absorbance of the transmitted signal is proportional to the path length L, this length should be closely controlled to minimize errors in reading the absorbance or signal "losses". By providing a flow cell body 12 having opposed transverse faces 36 and 38, the distance between which is closely controlled as determined by dimension D, and by providing probe bodies 60 having a closely controlled dimension "d" between the surfaces 83 and the surfaces 70, the path length L is closely controlled and the amount of error introduced into analysis of certain fluids by the analyzer 90 is minimized. Moreover, as indicated in the drawing FIGURE, the waveguide windows 82 project slightly beyond the transverse end faces of the body portions 62 and into the passage 22. In this way, the faces 83 are continuously scoured by the fluid flowing through the passage 22 to minimize contamination or clouding of these faces.

Accordingly, by controlling the dimension D between the faces 36 and 38 on the body 12 and by controlling the dimension d between the surfaces 70 and 83, the path length L is tightly controlled and errors due to changes in path length and light absorbance caused thereby are minimized with the improved apparatus 10. By way of example, if the dimension "D" is 4.060 inches with a tolerance of ±0.001 inches and the dimension "d" is 1.833 inches with a tolerance of ±0.001 inches, the maximum path length "L" will be 0.397 inches and the minimum 0.391 inches, which is a maximum path length error of only 1.5 percent. If the maximum absorbance of the signal passing from one probe member 46 to the other is 0.50 then the maximum absorbance difference due to path length tolerance is only 0.0075. It is also preferable that the bores 32 and 34 be held to a maximum eccentricity, with respect to each other, of about 0.002 inches.

As indicated above, the body 12 may be made of a suitably corrosion resistant metal or non-metallic material and the bodies 60 of the probes 46 may also be made of a suitable corrosion resistant metal or non-metallic material capable of withstanding the pressures and temperatures of fluid flowing through the passage 22, for example. Conventional manufacturing practices may be used in connection with fabricating the body 12 and the probes 46. The unique cylindrical optical elements or waveguide portions 82 and 86 may be of a type which are provided in a probe developed by Guided Wave, Inc. of Rancho Cordova, Calif., and described in Instrument Society of America, Paper No. 85-0033 and entitled "An In-Line Scanning UV/NIR Process Monitor"

by David A. LeFebre. The type of process analyzer which may be used as the analyzer 90 may be of a type described in U.S. Pat. No. 4,664,522, issued May 12, 1987 to David A. LeFebre.

Although a preferred embodiment of a flow cell and probe apparatus for use in spectrophotometer type analyzers has been described in some detail herein, those skilled in the art will recognize that various substitutions and modifications may be made to the apparatus without departing from the scope and spirit of the invention as recited in the appended claims.

What is claimed is:

1. Apparatus for determining certain properties of a flowable material, said apparatus comprising:

a flow cell body including first and second perpendicular intersecting bores having support surfaces, means for introducing said flowable material into one end of said first bore for flowing therethrough; and two probe means extending on opposite sides, respectively, of said first bore which respectively engage corresponding surfaces of said second bore for precisely locating each probe means with respect to said second bore and said oppositely disposed probe, said probe means being supported in said second bore in a predetermined position relative to said first bore for transmitting a signal through said flowable material in a predetermined portion of the spectrum of electromagnetic radiation, a portion of at least one of said probe means having a window extending into said first bore for allowing said flowable material to continuously scour said window to minimize contamination and clouding of said window.

* * * * *